United States Patent [19]
McMurray

[11] Patent Number: 4,745,912
[45] Date of Patent: May 24, 1988

[54] ORTHOPEDIC CASTING BANDAGE

[75] Inventor: Arthur W. McMurray, Aberdeen, N.C.

[73] Assignee: McMurray Fabrics, Inc., Aberdeen, N.C.

[21] Appl. No.: 933,737

[22] Filed: Nov. 21, 1986

[51] Int. Cl.⁴ .............................................. A61F 5/04
[52] U.S. Cl. ..................................... 128/90; 128/157; 66/193; 66/202; 428/254
[58] Field of Search ...................... 66/172 R, 193, 190, 66/191, 192, 202; 128/89 R, 90, 91 R, 156, 157, 169; 428/193, 254; 604/358, 370, 384

[56] References Cited

U.S. PATENT DOCUMENTS

| | | | |
|---|---|---|---|
| 2,578,889 | 12/1951 | Kennedy | 66/147 |
| 2,594,521 | 4/1952 | Tingley | 28/73 |
| 2,811,029 | 10/1957 | Conner | 66/202 |
| 3,340,134 | 9/1967 | Porter et al. | 604/384 |
| 3,557,156 | 1/1971 | Enneper et al. | 604/358 |
| 3,611,755 | 2/1970 | Millar | 66/173 |
| 3,654,056 | 4/1972 | Nisbet et al. | 161/62 |
| 3,686,725 | 8/1972 | Nisbet et al. | 28/74 R |
| 3,787,272 | 1/1974 | Nisbet et al. | 161/89 |
| 3,793,686 | 2/1974 | Nisbet et al. | 28/75 R |
| 3,882,857 | 5/1975 | Woodall, Jr. | 128/90 |
| 4,134,397 | 1/1979 | Gianakakos et al. | 128/90 |
| 4,320,634 | 3/1982 | Hashimoto et al. | 66/202 |
| 4,323,061 | 4/1982 | Usukura | 128/90 |
| 4,501,782 | 2/1985 | Weatherly et al. | 428/193 |
| 4,502,479 | 3/1985 | Garwood et al. | 128/90 |
| 4,609,578 | 9/1986 | Reed | 428/76 |

FOREIGN PATENT DOCUMENTS

2614905  4/1976  Fed. Rep. of Germany ........ 66/193

Primary Examiner—Richard J. Apley
Assistant Examiner—Paul Prebilic
Attorney, Agent, or Firm—B. B. Olive

[57] ABSTRACT

An orthopedic casting bandage and method is directed to a narrow width, warp-knit fabric formed in a relatively open knit construction of chain-stitched fiberglass yarn loops connected by laid-in fiberglass yarns running adjacent laid-in thermoplastic yarns. Widthwise sections are heat bonded at equal incremental lengths providing cut lines and, when cut, form individual casting bandages with substantially non-raveling, non-fraying and substantially flexible leading and trailing ends.

12 Claims, 5 Drawing Sheets

ORTHOPEDIC CASTING BANDAGE

TECHNICAL FIELD

The invention relates to an improved fabric bandage for making a water-activated, resin-impregnated, orthopedic cast.

BACKGROUND ART

An orthopedic cast according to a relatively recently introduced practice is formed by first placing a protective sleeve over the body member and then wrapping the protective sleeve with a padding to provide cushioning of the body member. A roll of flexible, warp-knitted, fiberglass fabric webbing impregnated with a water-activated casting material is wet with water, unrolled and wrapped around the body member. The water activated system sets and hardens and thereby forms the cast.

Fiberglass yarns used in making orthopedic casting bandages incorporate some type of finish or binder, typically a starch size, which holds the individual fibers together and facilitates both processing in manufacture and knitting. When the fabric is heat cleaned at a typical temperature cycle up to 750° F. to remove the starch prior to being impregnated with the water-activated casting material, the fabric tends to set and lose some of its desired stretch character in the final impregnated bandage product. U.S. Pat. No. 3,654,046 provides background information on heat cleaning and its effect.

A more recent practice has been to utilize the bandage fabric without heat cleaning and to impregnate the fabric with a water-activated resin impregnated casting material compatible with the presence of one and one-half to two percent by weight starch finish in the yarn. It has been found possible to package a roll of such fabric without fear of hardening in the typical air and liquid impervious sealed foil pouch used to hold the bandage preparatory to use. A two-bar, warp knit fabric of acceptable stretch character made entirely of non-heat cleaned fiberglass fabric with a compatible water-activated resin impregnated casting material was previously developed and has been successfully marketed under the trademark K-Cast by the Kirschner Medical Corporation of Timonium, Md.

Figure 1:
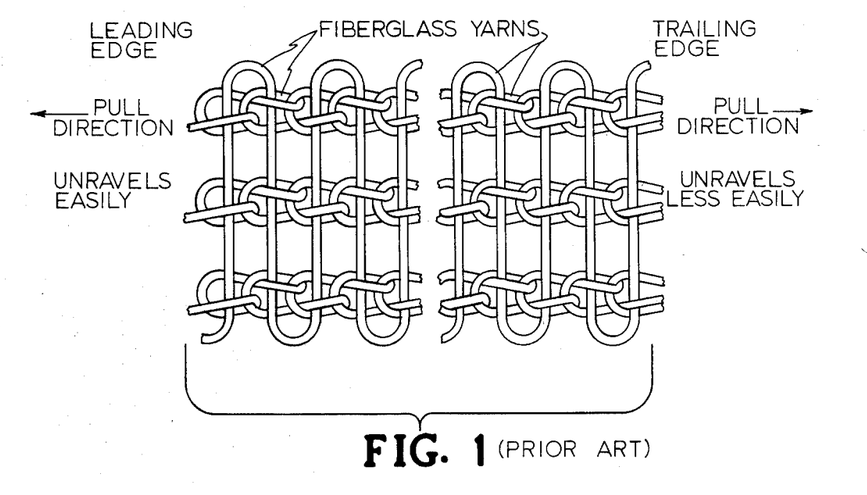
FIG. 1 is a fabric diagram looking at the technical back of a prior art bandage fabric indicating the relative ease of the leading and trailing edges to unravel and fray.

Warp knit casting bandage fabrics, as with many other knit fabrics, tend to unravel and fray particularly at the leading edge. This is illustrated in FIG. 1 showing the prior art two-bar, all-fiberglass, warp knit casting bandage construction having this undesired characteristic. While having a somewhat lesser tendency to unravel and fray, the trailing edge of such a bandage also has a tendency to unravel and fray as also illustrated in FIG. 1. Since casting bandage fabric is knit in a long length and then cut to the length of the individual casting bandage, the unravelling and fraying problem is severe on both the leading and trailing ends of each length of casting bandage. While an all-polyester, warp knit casting bandage has been employed with less of an unraveling and fraying problem, such a casting bandage lacks the desirable characteristics of a fiberglass yarn-based casting bandage.

Heat-cleaned, fiberglass casting bandage fabric, while introducing an undesirable stretch characteristic, nevertheless has tended to provide a relatively tight fabric having relatively less tendency to unravel and fray. On the other hand, the two-bar, fiberglass, warp-knitted, non-heat cleaned casting bandage fabric while having a desirable stretch characteristic has introduced the undesirable tendency to unravel and fray easily at both ends but particularly at the leading end. U.S. Pat. No. 4,609,578 discusses the fraying problem and emphasizes the importance to the trade of finding a satisfactory solution. However, it is noted that the process set forth in the patent to reduce unravelling and fraying requires heating the entire fabric to 1000° F. and exposure to such high heat, while well below the melting point of fiberglass yarns which is substantially above 1000 F., is nevertheless known to increase stiffness and cause embrittlement of the fabric.

The present invention provides both a unique casting bandage construction and yarn bonding technique for eliminating the unraveling and fraying problem. Therefore, reference is next made to prior art bonding practices with knitted fabrics.

Heat bonding of thermoplastic threads on edge portions of warp-knitted fabric is taught in U.S. Pat. Nos. 2,578,889 and 4,320,634. U.S. Pat. No. 2,578,889 teaches adhering together those threads forming warp knit fabric edges to prevent curling during processing and before the edges are trimmed. Such process prevents curling but produces an inherently stiff fabric which is not desirable for use as a casting bandage. U.S. Pat. No. 4,320,634 relates to a relatively stiff warp knit hem tape with thermoplastic yarns in the edges but whose characteristics are not suited to use as a casting bandage. U.S. Pat. No. 2,594,521 teaches heating an entire flatbed knitted fabric to bond the stitches together and which produces an overall stiff fabric unsuited for use as a casting bandage. U.S. Pat. Nos. 2,811,029 and 3,611,755 teach circular knit hosiery fabric in which a thermoplastic yarn is introduced into a selected portion of the fabric, then heated to bond together the stitches formed from another yarn of higher melting temperature to prevent runs. Such non-run hosiery fabric however is not suitable for use as a casting bandage because of the lack of selvages, because of lack of sufficient body in the fabric and because of the stiffness introduced. U.S. Pat. No. 3,142,109 teaches use of a heat sensitive plasticizer to bond fabric yarns together. While not illustrated in this last-mentioned patent, reference is made to warp knit fabric used for ordinary bandages. However, since the entire fabric is heat bonded, it would be expected that a substantially stiff fabric unsuited to use as a casting bandage would result.

The desired characteristics of a casting bandage are further discussed in U.S. Pat. Nos. 3,686,725; 3,787,272; 3,793,686; 3,882,857; and 4,502,479. Even though the desired characteristics of the conventional warp knit casting bandage fabric knit of fiberglass yarns have been identified, the problem of unraveling and fraying of the cut ends of the fabric has presented a recurring problem to the industry. While the prior art has also illustrated as described above warp knit fabric with edges formed by threads bonded together using thermoplastic yarn as well as warp knit fabric bonded throughout the fabric, the prior art has not provided a commercially-acceptable, non-unraveling, non-fraying, water-activated, resin-impregnated, flexible and body-conformable warp knit casting bandage using non-heat cleaned fiberglass fabric as the base fabric.

DISCLOSURE OF INVENTION

The invention as herein described in an illustrative embodiment provides a casting bandage formed of non-heat cleaned warp knit fabric made with chain-stitched wales formed solely of sized continuous filament fiberglass yarns interconnected with both inlaid thermoplastic and continuous filament fiberglass yarns extending widthwise of the fabric. The size may be starch as previously described. After knitting, the casting bandage fabric of relatively open knit construction is heat bonded in narrow widthwise sections at lengthwise intervals corresponding to the length of casting bandage desired. Such bonding tends to melt the thermoplastic yarns at the loop intersections and cause the melted plastic to flow, partially envelop, and bond the fiberglass yarns forming the chain stitch to the fiberglass yarns inlayed with the thermoplastic yarns. The end result is to prevent unraveling and fraying at both the leading end and trailing ends of the fabric once cut. The size on the fiberglass yarns tends to scorch where bonded and the visible scorch marks are utilized for defining where to cut for the lengths of bandage desired. Prior to cutting to length, the bandage is resin impregnated with a water activated curable resin, is then cut to length and suitably packaged in a moisture proof, air impervious, sealed package to prevent curing prior to use.

BEST MODE FOR CARRYING OUT THE INVENTION

The invention is directed both to a novel warp knit bandage construction and to the forming of individual casting bandages from such construction. The description first makes reference to knitting the bandage and later to forming the individual bandages.

Figure 2:
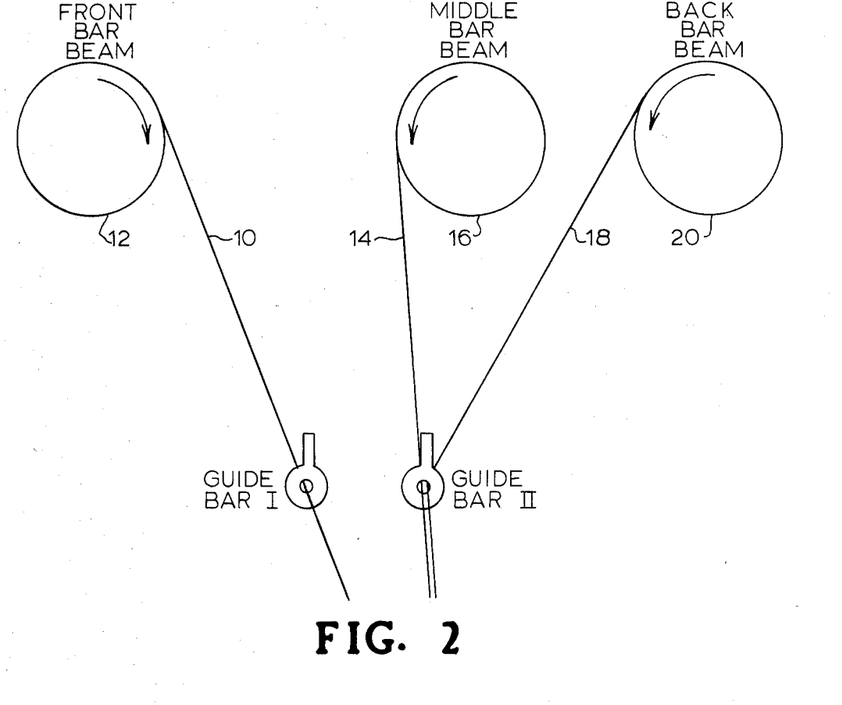
FIG. 2 shows the yarn beam positions on a three bar warp knitting machine used for the invention and illustrating the front and middle guide bars only being used with the front guide bar, designated guide bar I, carrying fiberglass yarn only and the middle guide bar, designated guide bar II, carrying both fiberglass and thermoplastic yarns.

The relatively narrow width invention fabric 20 is made on a single needle bar warp knitting machine 22 schematically illustrated in FIG. 2 as having a front guide bar, designated guide bar I, and a middle guide bar, designated guide bar II. Guide bar I is fully threaded with a fiberglass yarn 10 fed from a front bar beam 12. Guide bar II is fully threaded with both a fiberglass yarn 14 fed from middle bar beam 16 and with a thermoplastic yarn 18 fed from back bar beam 20. The yarn rate of feed of the back and middle bar beams are balanced to give a uniform lay-in. While full threading of both fiberglass yarns 10 and 14 and the thermoplastic yarn 18 is preferred, it has been discovered that when the thermoplastic yarn 18 is partially threaded to the extent of one in, one out, a highly flexible seal is obtained after bonding. It has also been discovered, however, that less partial threading of the thermoplastic yarn 18, as for example, one in, two out, tends to produce streaks and provides insufficient melt to prevent fraying. It is also desirable that the thermoplastic yarns comprise at least five percent (5%) by weight of the fabric 20.

Figure 3:
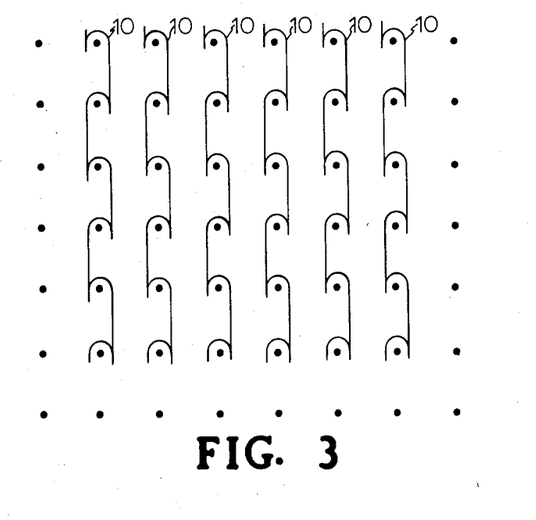
FIG. 3 is a stitch diagram for the front guide bar forming a chain stitch with fiberglass yarn.
Figure 4:
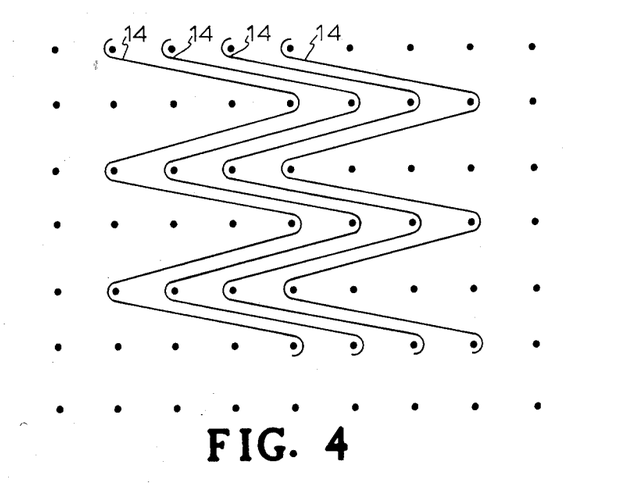
FIG. 4 is a stitch diagram for the middle guide bar making a four needle underlap with fiberglass yarn.
Figure 5:
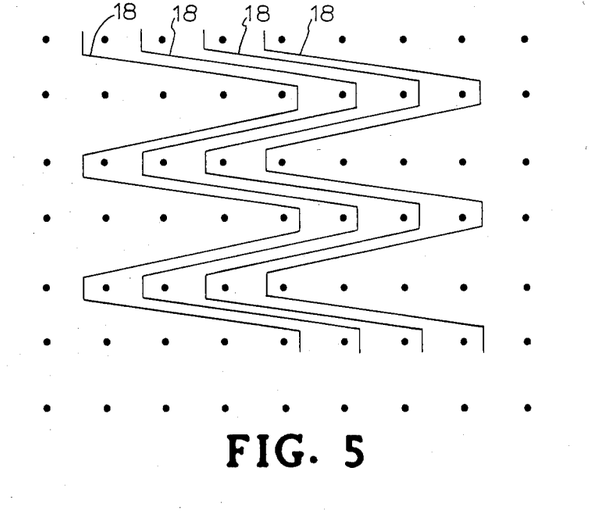
FIG. 5 is a stitch diagram for the middle guide bar making a four needle underlap with thermoplastic yarn.
Figure 6:
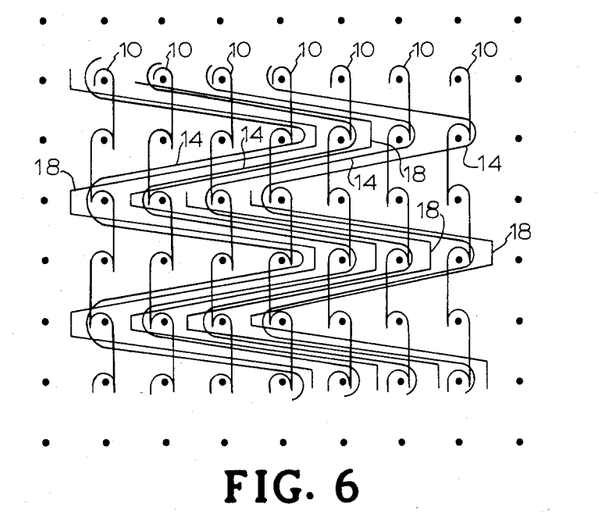
FIG. 6 is a stitch diagram combining the stitch diagrams of FIGS. 3, 4 and 5 to produce an illustrative preferred form of the invention fabric.
Figures 7, 10:
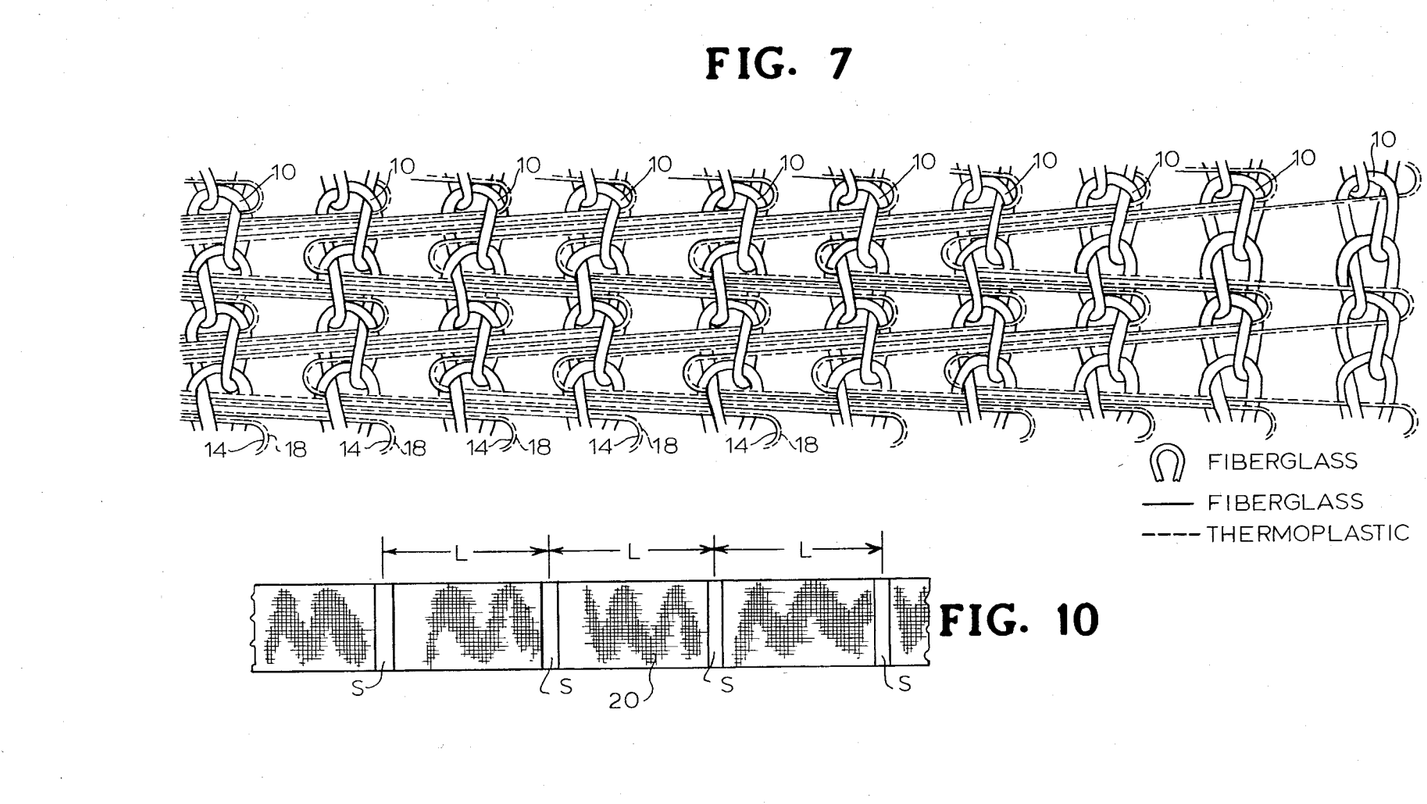
FIG. 7 illustrates the invention fabric of FIG. 6 enlarged for purpose of illustration and with the underlap fiberglass yarn and underlap thermoplastic yarn being shown in single solid and dashed lines respectively.
FIG. 10 is a schematic illustration of the lengthwise spaced heat seals made visible by the scorched size on the fiberglass yarn.

Guide bar I makes a chainstitch movement with the fiberglass yarn 10 on every course and in the example of FIG. 3 showing a six wale section follows a pattern 2-0, 0-2. In the same example, guide bar II follows the pattern 0-0, 8-8 and makes a four needle underlap. As best seen in the six course section of FIG. 4, fiberglass yarn 14 makes a four needle underlap. Likewise as seen in a similar six course section of the fabric in FIG. 5, thermoplastic yarn 18 also makes a four needle underlap. Thus, each underlap fiberglass yarn in the set of fiberglass yarns 14 as well as each thermoplastic yarn in the set of thermoplastic yarns 18 extend widthwise but for only a portion of the width of the fabric which may, for example, be 49 wales or approximately three inches in width. The complete fabric 20 of the example being illustrated is seen in a six wale section in FIG. 6. In FIG. 7, the same fabric is shown enlarged in a ten wale, four course section for better illustration of how the underlapped fiberglass yarns 14 and thermoplastic yarns 18 tend to lie in an essentially parallel and often side by side orientation. It has been discovered that a six-needle underlap provides insufficient width stretch in the casting bandage fabric 20 whereas a two needle underlap provides excess width stretch. Thus, a four-needle underlap, as used by way of example, is preferred. It has also been found that threading the thermoplastic yarn 18 in guide bar II only and not in guide bar I results in economies in yarn consumption, provides acceptable stretch and most importantly produces the desired non-unravelling and non-fraying edges.

In one example, fiberglass yarn 10 in guide bar I comprised Owens-Corning ECDE 100 1/0 1.0 Z fiberglass yarn as defined by trade terminology. Fiberglass yarn 14 in guide bar II also comprised ECDE 100 1/0 1.0 Z fiberglass yarn. Continuing with the same example, thermoplastic yarn 18 in guide bar II comprised Dupont 100/34/1 set textured, semi-dull, type 56, Dacron polyester yarn. Machine adjustments were made so that a flexible, loosely-knit fabric was obtained with approximately 30% lengthwise stretch and approximately 40% widthwise stretch.

In general, it has been found desirable to use fiberglass yarns 10, 14 having one turn per inch in the Z direction as indicated by the recited trade terminology.

It has also been found that the fiberglass filament diameter, in order to minimize an abrasive character, should preferably not exceed 0.00036 inches and for the overall purposes of the invention should not be less than 0.00015 inches. A diameter of 0.00025 inches is preferred. It has also been found that fiberglass yarn having a strand count of 37 to 150 provides an invention fabric of suitable weight and strength. A representative group of fiberglass yarns suited to the invention are designated as follows:

| Filament Designation | Nominal Filament Diameter (inches) | Strand Count ($\times$ 100 = yds/lb) | Approximate Number of Filaments |
|---|---|---|---|
| DE | 0.00025 | 150 | 408 |
| DE | 0.00025 | 100 | 600 |
| DE | 0.00025 | 75 | 816 |
| DE | 0.00025 | 37 | 1632 |

The thermoplastic yarn 18 is preferably a synthetic, polymeric, single-ply, multifilament set or stretch textured type yarn such as set textured polyester it also having been discovered that flat or non-textured thermoplastic gives unsatisfactory results. A 100/34/1 set textured polyester yarn produced better results than did a 70/34/1/ set textured polyester yarn. Any thermoplastic yarn 18 having the suitable melt character could be employed such as acrylic, nylon, polyester, polyvinyl chloride, polypropylene or polyethelene in set or stretch textured, bulk or spun form. What is most desirable is a thermoplastic yarn which in the described warp knit construction tends to flow when melted but which does not completely envelop the fiberglass yarns thus leaving the bonded fabric seals S (FIG. 10) pliable particularly in the widthwise direction as was obtained in the illustrative example.

Of particular significance to the invention is the fact that in the illustrative fabric 20 thermoplastic yarn 18 had a melting point of 382° F. which is substantially below the melting point of fiberglass yarns 10 and 14. As best seen in FIG. 7, it will be noted that in the illustrated example, plural strands of the thermoplastic yarns 18 are trapped adjacent the chainstitch loops formed by the fiberglass yarn 10. Thus, substantial, meltable thermoplastic material is available to bond the fiberglass yarns 10 and 18 together at the loop formations as next explained.

Figure 8:
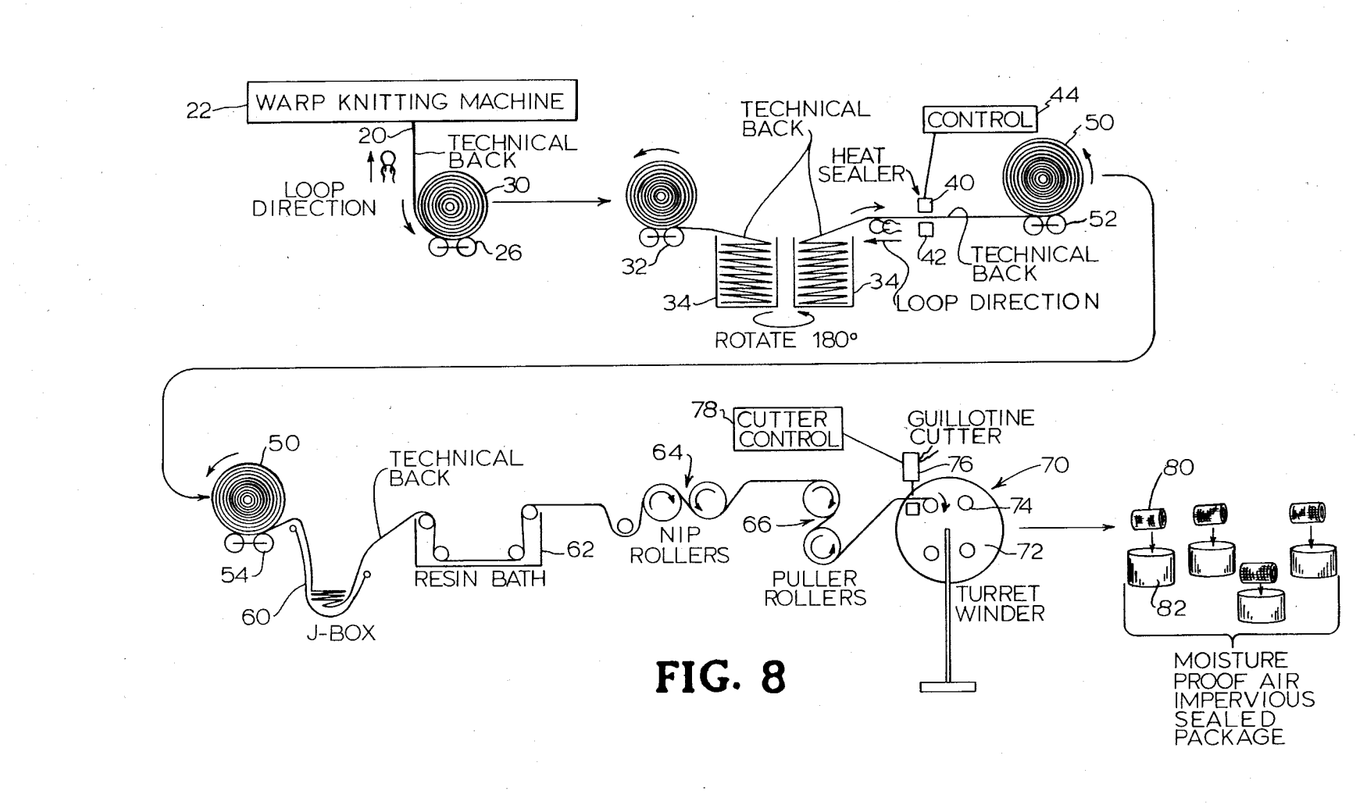
FIG. 8 illustrates in a flow diagram the steps related to knitting, heat sealing, impregnating and packaging of the bandage fabric of the invention according to a first embodiment.

Making reference next to FIG. 8, the improved invention fabric 20 of the invention in the illustrated example is knit on a single needle 3-bar Raschel warp knitting machine 22 as a continuous strip of fabric 20 and is initially rolled by a suitable surface drive winder 26 or other appropriate winding means into a roll 30 with the loop direction and technical back oriented as indicated. The so-called "technical back" and "technical face" are as defined in "An Introduction To The Stitch Formations In Warp Knitting", pages 101 and 103, published in 1966 by Employees Association of Karl Mayer, e.V. In order to maintain the leading edge and technical back suitably oriented for later heat sealing and packaging, the roll 30 is unrolled by a surface drive winder 32 or other means into a storage can 34. Can 34 is then rotated 180° following which the fabric 20 is unrolled and passed between a bar heat sealer 40 and supporting heat pad 44. Sealer 40 is controlled by a suitable control 42 such that as fabric 20 is intermittently withdrawn and re-rolled into another roll 50 by a surface drive winder 52 or other means, a heat seal S is impressed widthwise of fabric 20 at evenly spaced intervals corresponding to the individual bandage length L as schematically illustrated in FIG. 10. It has been discovered as previously mentioned that the size when in the form of starch, on the fiber glass yarns tends to scorch when heat sealed and the scorch marks are typically darker in color than the fiberglass yarns. Thus, visible and useful marks are advantageously provided at the desired intervals of cut and such marks have also been found to remain visible for use as cutting guidelines even after impregnation and to be aesthetically acceptable in the finished bandage.

Heat seal bar 40 in the example being described comprised an electrically-heated, Teflon-covered steel bar supported and operated by a pair of air cylinders, not shown. Pad 42 comprised a Teflon-covered rigid bar. When operative sealer bar 40 was heated to a temperature of 535° F. and formed a seal S of $\frac{1}{4}$" width W across the width of the fabric and with pressure applied by the air cylinders to slightly compress the fabric 20. Seals S (FIG. 10) were made at four yard intervals corresponding to the desired length L of the finished bandage 80. A range of settings was employed and it was discovered that with both full threading or one in, one out threading of thermoplastic yarn 18 exceptionally good results were obtained using the illustrated knit construction and illustrative example when the heat sealing dwell time was within the range of two to three seconds. A pliable seal, an aesthetically acceptable light tan seal mark and excellent thermoplastic flow were obtained within such time range.

With continuing reference to FIG. 8, roll 50 is next unrolled by surface drive winder 54 or other means and fed through a conventional J-box 60 from which the fabric 20 is pulled through a resin impregnating bath 62, through nip rollers 64, through puller rollers 66 and then to a suitable winding and cutting means 70 for winding and cutting individual lengths of the casting bandage. The seals S remain visible and aesthetically acceptable after impregnation and it is preferred that such seals S be formed before impregnation. A conventional four turret, variable speed winder 72, having four winding spindles 74 and equipped with an air operated guillotine cutter 76 with a suitable control 78 is illustrated as suitable for the purpose.

In operation, guillotine cutter 76 is activated after each spindle 74 is loaded with a suitable length of the now impregnated casting bandage. Each respective cut is taken through the center of a respective seal S. The individual impregnated casting bandage roll 80 is removed from the spindle and loaded in a moisture and air impervious foil pouch 82 after which the upper pouch edges are sealed. The illustrated process allows the finished bandage product 82 to be suitably rolled so that when unrolled there is provided a ravel- and fray-resistant edge at both the leading and trailing edges of the fabric. Since the fabric is applied with the technical face of the fabric on the outside of the cast and starting with a leading end of the bandage the loop direction and technical face are maintained in a corresponding orientation on winder 72 to allow the finished bandage 80 to be unrolled in this manner. The resin with which the casting bandage 80 is impregnated is of course activated with water to form a relatively rigid cast as well known in the art. However, prior to forming such cast, the impregnated fabric 20 presents the desired non-raveling, non-fraying and relatively-flexible, leading and trailing edges long sought in the industry in a fiberglass based casting fabric.

Figure 9:
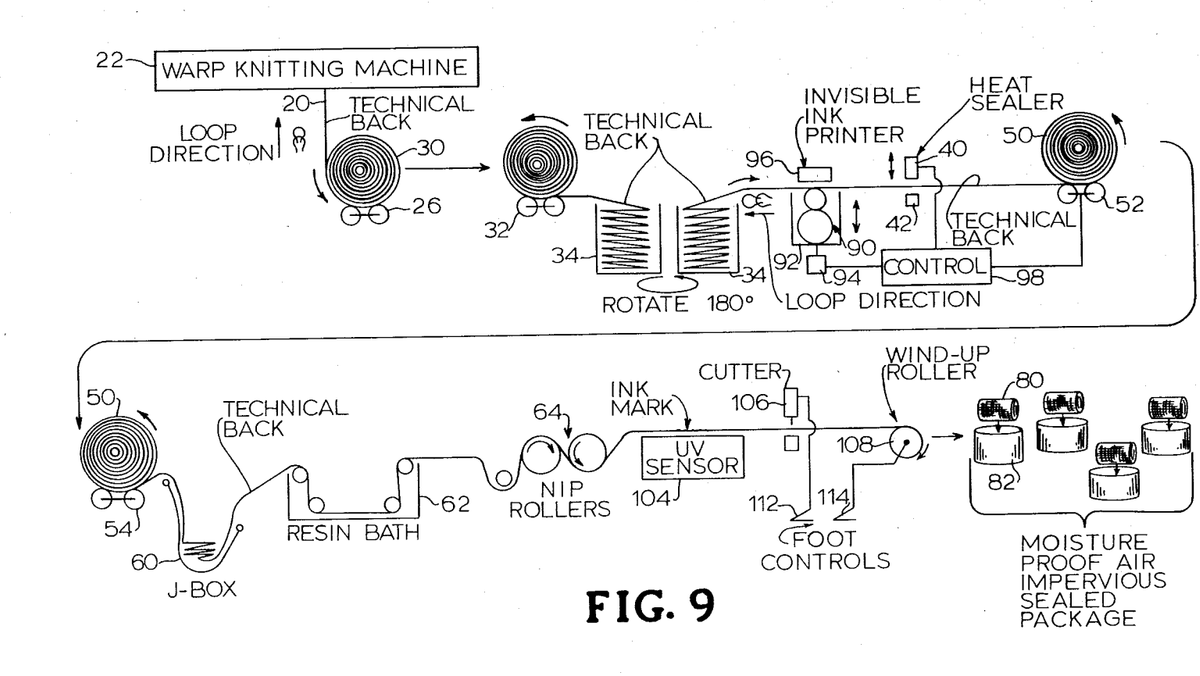
FIG. 9 illustrates in a flow diagram the steps related to knitting, heat sealing, applying a detectable mark with invisible ink, impregnating and packaging of the bandage fabric of the invention according to a second embodiment.

FIG. 9 represents in a flow diagram form a second embodiment for marking each seal S with an invisible mark detectable with an ultraviolet sensor. Making reference to FIG. 9, a conventional set of printing rollers 90 in an inkwell 92 are raised up and down by an actuator 94 under a suitable control 98 which also controls the surface drive winder 52. In operation, the fabric 20 is both sealed and marked at intervals L corresponding to the desired length of casting bandage. The ink employed is of a type commonly used in textile operations and is detectable by an ultraviolet (UV) sensor 104 such that cutter 106, and motor driven wind-up roller 108 can be controlled by foot controls 112, 114.

In summary, the invention offers the following significant advantages to the art:

1. A casting bandage having substantially no tendency to unravel or fray at either the leading or trailing end.
2. A casting bandage which does not require that the fiberglass fabric of which the casting bandage is made be subjected to the exceptional high heat cleaning temperature and process as in the prior art.
3. A casting bandage which can be readily cut apart at visibly observable marks formed as part of a heat bonding process which takes advantage of the binder.
4. A casting bandage adapted to be knit with a conventional warp knitting machine.
5. A casting bandage in which only the leading and trailing edges are exposed to a relatively low bonding heat leaving both the overall fabric as well as the leading and trailing edges flexible and conformable.
6. A casting bandage construction that uniquely utilizes thermoplastic yarns to create substantially non-raveling, non-fraying, flexible edges.

What is claimed is:

1. An elongate anti-raveling, anti-fraying, warp-knitted orthopedic casting bandage fabric comprising:
   (a) a first set of continuous multifilament fiberglass yarns forming lengthwise extending chains of spaced-apart loops;
   (b) a second set of lengthwise spaced apart inlay continuous filament fiberglass yarns extending widthwise of the fabric and interlaced with said chains of loops;
   (c) a third set of lengthwise spaced-apart inlay thermoplastic yarns contributing at least about five percent of the fabric weight and having a melting temperature substantially below the heat cleaning temperature for a fabric formed of said fiberglass yarns and extending widthwise of the fabric, said thermoplastic yarns of said second set being laid in with and running immediately adjacent said fiberglass yarns of said second set and also interlaced with said chains of loops to form an open knit construction, the extent of inlay for yarns in said second and third sets being substantially less than the width of said fabric and within the range of a two to six needle underlap; and
   (d) a series of narrow widthwise extending sections of fabric oriented perpendicular to the lengthwise direction of and equally spaced apart lengthwise of the fabric and containing a melt of said thermoplastic yarns so as to at least partially envelop said first and second sets of said fiberglass yarns in said sections such that when said sections are cut through individual casting bandages are formed with substantially flexible, non-raveling, non-fraying, leading and trailing edges thereof.

2. A casting bandage fabric as claimed in claim 1 wherein said fabric constitutes a single-needle, 3-bar warp knit fabric.

3. A casting bandage fabric as claimed in claim 1 wherein said fiberglass yarns are covered with a finish which tends to darken when said thermoplastic yarns are melted making said sections visible.

4. A casting bandage fabric as claimed in claim 1 wherein said thermoplastic yarns comprise textured yarns.

5. A casting bandage fabric as claimed in claim 1 wherein individual filaments in said first and second sets of fiberglass yarns have a diameter within the range of 0.00015 to 0.00036 inches and said fiberglass yarns have a strand count of 37 to 150.

6. A casting bandage fabric as claimed in claim 1 wherein said thermoplastic yarns are selected from the group consisting of set-textured, stretch-textured, spun or bulk synthetic thermoplastic yarns.

7. A casting bandage fabric as claimed in claim 1 wherein the extent of inlay for yarn in said second and third sets is equal.

8. A resin-impregnated, warp-knitted elongate casting bandage comprising:
   (a) a warp-knitted casting bandage fabric formed of chains of spaced-apart loops of fiberglass yarns joined by widthwise extending thermoplastic and fiberglass yarns, said thermoplastic yarns comprising at least about five percent of the weight of the fabric and said widthwise extending yarns being inlayed together with the extent of inlay for individual yarns being within the range of two to six needle underwrap and extending less than the width of the fabric, said thermoplastic yarns being heat bonded at widthwise extending railing and leading edges of the casting bandage and said thermoplastic yarns melted at a temperature substantially below the heat cleaning temperature of a fabric formed of said fiberglass yarns and with the melt thereof being employed to bond said fiberglass yarns together to prevent unravelling and fraying of said edges;
   (b) a liquid resin impregnating said casting bandage and capable of curing to form a rigid cast; and
   (c) a package for said casting bandage to prevent curing of said casting bandage prior to use.

9. A casting bandage as claimed in claim 8 in which the diameter of individual filaments in said fiberglass yarns are within a range of 0.00015 to 0.00036 inches and said fiberglass yarns have a strand count of 37 to 150.

10. A casting bandage as claimed in claim 8 wherein said thermoplastic yarns are selected from the group consisting of set-textured, stretch-textured, spun or bulk synthetic thermoplastic yarns.

11. A casting bandage as claimed in claim 8 wherein said fiberglass yarns are covered with a finish which tends to darken when said thermoplastic yarns are melted.

12. A casting bandage as claimed in claim 8 wherein said extent of inlay for both said thermoplastic and fiberglass inlay yarns is equal.

* * * * *

UNITED STATES PATENT AND TRADEMARK OFFICE
CERTIFICATE OF CORRECTION

PATENT NO. : 4,745,912

DATED : May 24, 1988

INVENTOR(S) : Arthur W. McMurray

It is certified that error appears in the above-identified patent and that said Letters Patent is hereby corrected as shown below:

Column 8, line 39 correct --railing-- to read "trailing".

Signed and Sealed this

Eleventh Day of October, 1988

*Attest:*

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,745,912

DATED : May 24, 1988

INVENTOR(S) : Arthur W. McMurray

It is certified that error appears in the above-identified patent and that said Letters Patent is hereby corrected as shown below:

Column 7, line 54, replace "second" with --third--.

Signed and Sealed this

Nineteenth Day of April, 1994

*Attest:*

BRUCE LEHMAN

*Attesting Officer*    *Commissioner of Patents and Trademarks*